United States Patent [19]

Beck et al.

[11] 4,054,603

[45] Oct. 18, 1977

[54] 4-AMINO-3,5-DINITROBENZENESULFENA-MIDES AND SULFINAMIDES

[75] Inventors: James R. Beck, Indianapolis; Joseph A. Yahner, New Palestine, both of Ind.

[73] Assignee: Eli Lilly and Company, Indianapolis, Ind.

[21] Appl. No.: 719,294

[22] Filed: Aug. 31, 1976

[51] Int. Cl.$^2$ ............... C07C 145/00; C07C 145/02; A01N 9/12; A01N 9/14
[52] U.S. Cl. .................................. 260/551 S; 71/98; 71/103; 424/330
[58] Field of Search .................. 260/551 S, 556 B; 71/98, 103; 424/330

[56] References Cited

U.S. PATENT DOCUMENTS

| | | | |
|---|---|---|---|
| 2,244,075 | 6/1941 | Mikeska | 260/551 S X |
| 2,474,237 | 6/1949 | Eby | 260/551 S |
| 2,946,715 | 7/1960 | Stansbury et al. | 260/551 S X |
| 3,124,447 | 3/1964 | Wineman et al. | 71/98 X |
| 3,367,949 | 2/1968 | Soper | 71/103 X |
| 3,449,111 | 6/1969 | Wright | 71/103 X |
| 3,518,076 | 6/1970 | Wright | 71/103 X |
| 3,546,295 | 12/1970 | Maravetz | 260/556 B |
| 3,746,727 | 7/1973 | Pilgram et al. | 71/103 X |
| 3,752,661 | 8/1973 | Orlett | 260/556 B X |
| 3,772,277 | 11/1973 | Beck | 71/103 X |
| 3,786,048 | 1/1974 | Beck | 71/103 X |
| 3,829,487 | 8/1974 | Mrozik | 260/556 B X |
| 3,832,155 | 8/1974 | Beck | 71/103 |
| 3,840,569 | 10/1974 | Beck | 71/103 X |
| 3,875,192 | 4/1975 | Suhr | 71/103 X |
| 3,966,817 | 6/1976 | Pilgram | 71/103 X |
| 3,971,650 | 7/1976 | Schinski | 71/103 |
| 3,989,508 | 11/1976 | Fischer | 71/103 X |

*Primary Examiner*—Daniel E. Wyman
*Assistant Examiner*—Thomas A. Waltz
*Attorney, Agent, or Firm*—Dwight E. Morrison; Everet F. Smith

[57] ABSTRACT

A new class of 4-amino-3,5-dinitrobenzenesulfenamides and sulfinamides has been prepared. The new compounds possess a substituted amino group in the 4-position. Such compounds possess herbicidal activity and also activity against *Plasmopara viticola,* the causative agent of grape downy mildew.

3 Claims, No Drawings

4-AMINO-3,5-DINITROBENZENESULFENAMIDES AND SULFINAMIDES

BACKGROUND OF THE INVENTION

1. Field of the Invention

This invention relates to new chemical compounds. More particularly, this invention relates to 4-amino-3,5-dinitrobenzenesulfenamides and sulfinamides.

2. Description of the Prior Art

Various 2,6-dinitroanilines have been described in the chemical literature. Hantzsch, *Deutsche Chemische Gesellschaft Berichte*, 43, 1662–1685 (1910) discloses N,N-dipropyl-4-methyl-2,6-dinitroaniline and N,N-dimethyl-4-methyl-2,6-dinitroaniline. Joshi et al., C.A. 28, 469 (1934) disclose N,N-dimethyl-4-iodo-2,6-dinitroaniline, N,N-dimethyl-4-bromo- 2,6-dinitroaniline, 4-iodo-2,6-dinitrophenylpiperidine, and 4-bromo-2,6-dinitrophenylpiperidine. Borsche et al., C.A. 5, 2079 (1911) disclose 2,6-dinitrophenylpiperidine. Daudt et al. U.S. Pat. No. 2,212,825, disclose a number of 2,6-dinitroanilines bearing a trifluoromethyl group in the 4-position.

The utility of 2,6-dinitroanilines in agriculture was first disclosed in Soper U.S. Pat. Nos. 3,111,403; 3,257,190; 3,332,769; and 3,367,949. Soper disclosed such compounds to possess herbicidal activity, notably preemergent herbicidal activity. Following Soper, a large number of related dinitroanilines have also been shown to possess similar herbicidal activity. See, for example, U.S. Pat. Nos. 3,321,292; 3,617,251; 3,617,252; 3,672,864; 3,672,866; 3,764,624; and 3,877,924 and Belgian Pat. No. 787,939.

SUMMARY OF THE INVENTION

A new group of 4-substituted-3,5-dinitrobenzenesulfenamide and sulfinamide compounds having the formula

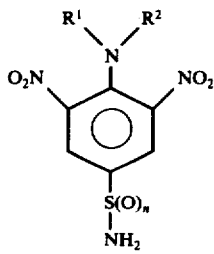

wherein
$R^1$ is hydrogen, $C_3$–$C_4$ alkenyl or $C_1$–$C_3$ alkyl;
when $R^1$ is hydrogen, $R^2$ is $C_3$–$C_7$ secondary alkyl;
when $R^1$ is not hydrogen, $R^2$ is $C_1$–$C_4$ alkyl; and
$n$ is 0 or 1.

These new compounds possess fungicidal activity against the causative organism of grape downy mildew. The compounds also possess herbicidal activity.

DESCRIPTION OF THE PREFERRED EMBODIMENT

In the above description of the novel compounds, all of the terms employed have the meanings normally ascribed to them in the chemical art.

The novel 4-amino-3,5-dinitrobenzenesulfenamide compounds are prepared from bis(4-substituted amino-3,5-dinitrophenyl)disulfides which are in turn prepared as taught by Cannon, U.S. Pat. No. 3,715,479 (Apr. 3, 1973). The sulfenamide compounds are prepared by treatment of the corresponding disulfide in the cold with silver nitrate followed by the bubbling in of gaseous ammonia, still in the cold, for a period of time sufficient to substantially complete the reaction. Such period of time is about 4 hours. The reaction mixture is then allowed to warm to room temperature and stirred overnight. The product is isolated by concentrating the reaction mixture in vacuo, taking the residue up in benzene and filtering. The solid material which is collected on the filter is washed with ether and discarded and the filtrate is concentrated in vacuo to leave a residue which is then purified by recrystallization or distillation and the product is identified by elemental analyses and NMR and IR spectra.

The novel 4-amino-3,5-dinitrobenzenesulfinamide compounds are then prepared from the corresponding sulfenamide compounds by oxidation with a suitable oxidizing agent, such as m-chloroperbenzoic acid, in an inert solvent, such as methylene chloride.

The following examples illustrate the preparation of the novel compounds, but such examples are not to be interpreted as placing any limit upon the scope of the invention.

EXAMPLE 1

To a cold solution of 1.7 g. (0.01 mole) of silver nitrate in 150 ml. of methanol there was added portionwise 6.0 g. (0.01 mole) of bis[4-di(n-propyl)amino-3,5-dinitrophenyl]-disulfide [prepared as taught by Cannon, U.S. Pat. No. 3,725,479 (Apr. 3, 1973)]. When the addition was complete, gaseous ammonia was bubbled into the solution for about 4 hours and an additional 0.5 g. of silver nitrate was added. Thin layer chromatography showed that there was a slight amount of starting material still remaining. The reaction mixture was stirred overnight at room temperature. The reaction mixture was then cooled and concentrated in vacuo. The residue was taken up in benzene and filtered. The solid material collected on the filter was washed with ether. The filtrate was concentrated in vacuo to leave a red oil, which solidified. The product weighed 2.4 g. and had a melting point of about 63°–65° C. It was identified by elemental analyses and NMR and IR spectra as 4-(dipropylamino)-3,5-dinitrobenzenesulfenamide.

Calculated: C, 45.85; H, 5.77; N, 17.82; S, 10.20.
Found: C, 45.59; H, 5.50; N, 17.62; S, 9.90.

EXAMPLE 2

To a solution of 1 g. (0.003 mole) of 4-(dipropylamino)-3,5-dinitrobenzenesulfenamide in 50 ml. of methylene chloride, there was added 0.56 g. (0.0032 mole) of m-chloroperbenzoic acid. The reaction mixture became slightly warm and it was stirred for about 15 minutes at ambient room temperature. Thin layer chromatography showed no starting material remained. The reaction product mixture was extracted twice with dilute aqueous sodium bicarbonate solution and then washed once with water. The washings were discarded and the organic layer was concentrated in vacuo to leave an oil which was eluted from a silica gel column with 1:1 ethyl acetate:hexane solvent. The first product obtained from the column was a disulfide compound. The second product isolated from the column was recrystallized from 95 percent ethanol to yield product having a melting point of about 125°–126° C., and was identified by elemental analyses and NMR spectrum as 4-(dipropylamino)-3,5-dinitrobenzenesulfinamide. Weight: 550 mg.

Calculated: C, 43.63; H, 5.49; N, 16.96. Found: C, 43.89; H, 5.31; N, 16.68.

The compounds of this invention are useful as herbicides, especially preemergent herbicides, and in the control of *Plasmopara viticola*, the causative organism of downy mildew of grape. The preferred compound for herbicidal use is 4-(dipropylamino)-3,5-dinitrobenzenesulfinamide.

The compounds are used as herbicides or fungicides in accordance with procedures well known in the agricultural art. For either use, the compounds are preferably employed in liquid, powder or dust compositions containing one or more of the active compounds. In preparing such compositions, the compounds can be modified with one or more of a plurality of additaments, including organic solvents, petroleum distillates, water, or other liquid carriers, surface-active dispersing agents, and finely divided inert solids. In such compositions, the active compound can be present in a concentration of from about 2 to about 98 percent by weight.

In the preparation of dust compositions, the active ingredient can be compounded with any of the finely divided solids, such as pyrophyllite, talc, chalk, gypsum, and the like. In such operations, the finely divided carrier is ground or mixed with the active ingredient, or is wet with a solution of the active ingredient in a volatile organic solvent. Similarly, dust compositions containing the active compound can be prepared with various solid surface-active dispersing agents, such as fuller's earth, bentonite, attapulgite, and other clays. Depending on proportions of ingredients, these dust compositions may be employed as such or may be diluted with an additional solid surface-active dispersing agent or with pyrophyllite, chalk, talc, gypsum and the like, to obtain a composition containing the desired amount of active ingredient. Also, such dust compositions can be dispersed in water with or without the aid of dispersing agents to form liquid sprayable mixtures. The compounds of this invention or a liquid or dust concentrate composition containing such active compounds can be incorporated in infinite mixture with surface-active dispersing agents, such as nonionic emulsifying agents, to form spray compositions. Such compositions may be employed as such or may be dispersed in liquid carriers to form dilute sprays containing the active compound in any desired amount.

Similarly, the compounds can be mixed with a suitable water-immiscible organic liquid and a surface-active dispersing agent to produce emulsifiable concentrates which can be further diluted with water and/or oil to form spray mixtures in the form of oil-water emulsions. Preferred dispersing agents to be employed in these compositions are oil-soluble and include the nonionic emulsifiers, such as condensation products of alkylene oxides with phenols, sorbitan esters, complex ether alcohols, and the like. Suitable organic liquids which can be employed include petroleum oils and distillates, toluene, and synthetic organic oils. The surface-active dispersing agents are usually employed in liquid compositions in the amount of from about 0.1 to about 20 percent by weight of the composition.

For herbicidal applications, the compounds are employed at a rate of from about 0.5 to about 10 kg./ha. The compounds are preferably employed as preemergence herbicides and may be sprayed onto the surface of the area to be treated or may be mixed into the soil. The compounds are useful in eliminating undesirable vegetation in areas where crops such as cotton and soybeans are grown.

When employed to control grape downy mildew, the compounds are employed at the rate of from about 10 g. to 2 kg. of active ingredient per hectare. The compounds are applied to the foliage of the grape plants as a liquid or dust spray. As is customary in such application, it may be necessary to apply the compounds more than once during the growing season.

We claim:

1. A compound selected from the group consisting of compounds of the formula

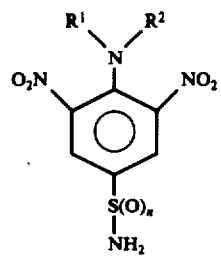

wherein
R$^1$ is hydrogen, C$_3$–C$_4$ alkenyl or C$_1$–C$_3$ alkyl;
when R$^1$ is hydrogen, R$^2$ is C$_3$–C$_7$ secondary alkyl;
when R$^1$ is not hydrogen, R$^2$ is C$_1$–C$_4$ alkyl; and
$n$ is 0 or 1.

2. A compound as in claim 1, such compound being 4-(dipropylamino)-3,5-dinitrobenzenesulfenamide.

3. A compound as in claim 1, such compound being 4-(dipropylamino)-3,5-dinitrobenzenesulfinamide.

* * * * *